United States Patent
Dullien

(10) Patent No.: US 6,174,665 B1
(45) Date of Patent: Jan. 16, 2001

(54) HORMONE REPLACEMENT THERAPY MONITORING

(75) Inventor: Vivian Dullien, Boulder, CO (US)

(73) Assignee: Biex, Inc., Dublin, CA (US)

( * ) Notice: Under 35 U.S.C. 154(b), the term of this patent shall be extended for 0 days.

(21) Appl. No.: 09/394,579

(22) Filed: Sep. 10, 1999

(51) Int. Cl.[7] ............................. C12Q 1/00; G01N 33/53
(52) U.S. Cl. ............................. 435/4; 435/975; 552/502; 552/605; 552/607
(58) Field of Search ..................... 435/4, 975; 552/502, 552/625, 607

(56) References Cited

U.S. PATENT DOCUMENTS

| | | | |
|---|---|---|---|
| 4,381,292 | 4/1983 | Bieber et al. | 435/4 |
| 4,451,570 | 5/1984 | Royston et al. | 435/4 |
| 4,618,577 | 10/1986 | Handley | 435/4 |
| 5,370,135 | 12/1994 | Dullien | 435/4 |
| 5,480,776 | 1/1996 | Dullien | 435/4 |
| 5,550,029 | 8/1996 | Simpkins | 435/4 |
| 5,786,227 | 7/1998 | Charlton | 435/4 |
| 5,786,228 | 7/1998 | Charlton | 435/4 |
| 5,932,431 * | 8/1999 | Williams et al. | 435/7.93 |
| 5,981,293 | 11/1999 | Charlton | 435/4 |

FOREIGN PATENT DOCUMENTS

| | | |
|---|---|---|
| WO 96/03929 | 2/1996 | (WO) . |
| WO 96/27800 | 9/1996 | (WO) . |

OTHER PUBLICATIONS

Tankersley et al; J. of Applied Physiology, V. 73(4), p. 1238–1245, 1992.*

Hammond, Climacteric (Chapter 42, pp. 771–790; in Danforth's Obstetrics and Gynecology, 7th edition, ed. Scott et al., JB Lipincott Co., Philadelphia, PA (1994).

Notelovitz, Contemporary Ob/Gyn, Feb. (1999), pp. 54–64.

Santoro, et al.,(1996), J. Clin. Endocrinol. Metab. 81: pp. 1495–1501.

Clinical Gynecological Endocrinology and Infertility, 4th ed., p. 155, Speroff, Glass, and Kase, eds., Williams and Wilkins (MD) (1989).

Clinical Gynecological Endocrinology and Infertility, 4th ed., p. 134, Speroff, Glass, and Kase, eds., Williams and Wilkins (MD) (1989).

Clinical Gynecological Endocrinology and Infertility, 4th edition, ed. Speroff et al., Williams and Wilkins (Baltimore, MD) p. 629, (1989).

Tietz, Textbook of Clinical Chemistry, 3rd ed., W.B. Saunders and Col. (Philadelphia, PA), pp. 1811–1814; 1831–1835; (1999).

Lasley, et al., Fertility and Sterility (1985), 43: pp. 861–867.

Munro, et al., Abstract No. 73, p. 117, Society for Gynecologic Investigation, San Diego, Mar. (1989).

* cited by examiner

*Primary Examiner*—Louise N. Leary
(74) *Attorney, Agent, or Firm*—David S. Harper; McDonnell, Boehnen, Hulbert & Berghoff

(57) ABSTRACT

The present invention provides methods for monitoring the effectiveness of hormone replacement therapy in a perimenopausal, early menopausal, or late menopausal woman, comprising testing for hormonal levels in a body fluid of the woman at intervals depending on the stage of menopause, and adjusting levels of replacement hormone administered to the woman based on the test results.

6 Claims, No Drawings

HORMONE REPLACEMENT THERAPY MONITORING

FIELD OF THE INVENTION

The invention relates to methods for monitoring the effectiveness of hormone replacement therapy in various stages of menopause.

BACKGROUND OF THE INVENTION

Menopause is a natural event in a woman's life that designates the end of fertility, and results from decreased ovarian production of estrogen and progesterone. In its strictest sense, menopause refers to a one-day event occurring one year after the last menstrual period. While the majority of women experience "natural" menopause, some women undergo "induced" menopause, due to any one of a number of medical interventions, such as surgical removal of the ovaries, or ovarian damage by radiation or chemotherapy.

Perimenopause refers to a period of up to 7 years wherein the woman has wide fluctuations in estrogen levels from month to month. Perimenopause generally starts when a woman is in her forties, and ends one year after menstruation stops. During perimenopause, a woman may be in estrogen deprivation one month but not the next. She may experience symptoms of menopause, such as hot flashes and insomnia, which also may fluctuate from month to month. During perimenopause, a diagnosis of estrogen deprivation may be accurate one month and proper hormone replacement therapy ("HRT") prescribed, while the next month the HRT dosage may be too much or not enough.

Early menopause/post-menopause (hereinafter referred to as "early menopause") refers to the 10-year period starting one year after menstruation ceases, when women are typically in their 50's to early 60's. During early menopause, estrogen levels tend to be consistently low, although lifestyle changes, disease, weight gain or loss exercise increase or decrease, and/or stress may change the optimal HRT dosage.

Late menopause/post menopause (hereinafter referred to as "late menopause") occurs at age 65 and beyond. Little is known about estrogen metabolism in aged women, and it may differ significantly between a 70 year old and a 90 year old woman. Lifestyle changes, disease, weight gain or loss, exercise increase or decrease, aging, and/or stress may change the optimal HRT dosage, which may decrease in very old women.

The principal circulating estrogen in pre-menopausal women is estradiol-17$\beta$. Estradiol is produced either by direct ovarian secretion or by peripheral conversion of testosterone and estrone.

The predominant estrogen of post-menopausal women is estrone. (Hammond, Climacteric (Chapter 42, pp. 771–790; in Danforth's Obstetrics and Gynecology, 7th edition, ed. Scott et al., JB Lippincott Co., Philadelphia, Pa. (1994). The biological potency of estrone is only one third that of estradiol. The post-menopausal ovary and adrenal gland produce virtually no estrone. Production rates post-menopausally are 40 $\mu$g/day for estrone and 6 $\mu$g/day for estradiol, compared with 80–500 $\mu$g/day for estradiol and 80–300 $\mu$g/day for estrone in reproductive-aged women. (Hammond, 1994)

Virtually all estradiol in post-menopausal women can be accounted for by the conversion of estrone. (Hammond, 1994) Testosterone production in the menopausal woman remains constant, but only about 0.1% of testosterone is converted to estradiol. Testosterone levels in post-menopausal women decline, but not to the same extent as estrogen levels.

Prescription estrogen replacement therapy has been widely used for many years for treating menopause-related disturbances. However, estrogen therapy is still very much a "hit-or-miss" treatment. (See U.S. Pat. No. 5,550,029, incorporated by reference herein in its entirety.) The approach to HRT is routine and empiric. Treatment is initiated with traditional doses, and if the woman does not respond, the dose is increased without evaluating the reason for HRT non-effectiveness. (Notelovitz, Contemporary Ob/Gyn, February 1999 pp. 54–64)

The dosage administered is typically determined based on the results of annual testing, without regard to what stage of menopause a woman is in, and despite the fact that estrogen levels often vary widely from month to month in perimenopausal women. (See for example, Notelovitz, February 1999; Santoro et al., J. Clin. Endocrinol. Metab. 81:1495–1501 (1996). Furthermore, some authorities assert that they "find no need to monitor dosage by any means other than symptoms and bleeding. (From Clinical Gynecological Endocrinology and Infertility, 4th ed., p. 155, Speroff, Glass, and Kase, eds., Williams and Wilkins (MD) 1989) In addition, the HRT protocol may be adversely affected by transient side effects that can be short term (such as nausea or bloating) or long term (such as increased susceptibility to cancer).

Thus, traditional HRT therapy with annual testing is frequently ineffective. As a direct result of this lack of success, it is estimated that only 15% of post-menopausal women currently receive estrogen therapy, and that as many as 80% of women discontinue HRT after initiating treatment. The uncertainty associated with the outcome of long term HRT, as well as the frequent ineffectiveness of treatment, results in unnecessary health care costs, postponement of the potential benefits of alternative treatments such as dietary supplements, and a certain risk of side effects such as increased susceptibility to breast and endometrial cancers, hypertension and gall bladder disease with no actual benefit to offset the risk for the patient. Furthermore, women who respond well to estrogen may be able to benefit from a reduced dosage. There are many types of estrogens on the market and many more in research and development. It is possible that one type of estrogen may be better suited to an individual's needs than another.

The population of postmenopausal is increasing. It is estimated that women in the United States now live approximately one-third of their lives after menopause. Thus, the problems of the perimenopausal, early and late menopausal periods have achieved the status of a major public health concern. (From Clinical Gynecological Endocrinology and Infertility, 4th ed., p. 134, Speroff, Glass, and Kase, eds., Williams and Wilkins (MD) 1989) Estrogen deprivation is associated with many problems, including osteoporosis and increased risk of heart disease.

Therefore, a new approach to evaluate the effectiveness of HRT, which takes into account the menopausal stage and corresponding fluctuation in hormone levels, would have utility in therapy planning by reducing the uncertainty now associated with the outcome of long-term HRT.

SUMMARY OF THE INVENTION

The present invention provides methods for monitoring the effectiveness of hormone replacement therapy in a perimenopausal, early menopausal, or late menopausal woman, comprising testing for hormonal levels in a body fluid of the woman at intervals depending on the stage of menopause, and adjusting levels of replacement hormone administered to the woman based on the test results. In a preferred embodiment, the test is done on saliva.

DETAILED DESCRIPTION OF THE PREFERRED EMBODIMENTS

The methods of the present invention provide for more aggressive monitoring of the effectiveness of hormone replacement therapy, and thus are useful not only for alleviating the symptoms of menopause such as depression, hot flashes, insomnia, and decreased sexual drive, but also will improve the protective effects of hormone replacement therapy against osteoporosis and heart disease.

As used herein, the term "menopausal woman" refers to women in any of the menopausal stages herein discussed, including perimenopause, menopause, early menopause, and late menopause.

As used herein, the term "hormone replacement therapy" encompasses treatment with estrogen or estrogen analogs alone, or in combination with progesterone or other hormones As used herein, the term "perimenopause" refers to a period of up to 7 years that generally stats when a woman is in her forties, wherein has wide fluctuations in estrogen levels from month to month. Perimenopause ends one year after menstruation stop.

As used herein, the term "menopause/post-menopause" (hereinafter referred to as "early menopause") refers to the 10-year period starting one year after menstruation ceases, when women are typically in their 50's to early 60's.

As used herein, the term "late menopause/post menopause" (hereinafter referred to as "late menopause") occurs at age 65 and beyond.

In one aspect, the method comprises varying the frequency of monitoring HRT effectiveness based on the menopausal stage that a patient is in, and the adjusting the HRT dosage based on the results of the testing.

In a preferred embodiment, the hormonal level of a perimenopausal woman would be monitored between about every week to about every 3 months. In a most preferred embodiment, the hormonal level of a perimenopausal woman would be monitored on a monthly basis and HRT dosage would be tailored based on these hormonal measurements. This contrasts with the standard clinical practice of testing at annual obstetrics/gynecological examinations and prescribing a fixed dosage for one year.

In another preferred embodiment, the hormonal level of a woman in early menopause or late menopause or would be monitored Between about every month to about every 6 months, and HRT dosage would be tailored monthly based on the hormonal measurements. This contrasts with the standard clinical practice of testing at annual obstetrics/gynecological examinations and prescribing a fixed dosage for one year.

In each case, the methods of the invention deviate from the standard clinical practice of testing at annual obstetrics/gynecological examinations, and prescribing a fixed dosage for one year that does not take into account fluctuations in a woman's hormonal level in perimenopause, or changes in hormonal level in aged women. The more frequent hormone testing and adjustment of HRT dosages of the present invention allows for a better titrated HRT than is possible with prior art methods.

In a preferred embodiment, the level of estradiol in the body fluid of a menopausal woman is measured as an indicator of the effectiveness of HRT. In further preferred embodiments, the levels of progesterone, testosterone, and/or estriol in the body fluid are also measured.

In this invention, there are no limitations on the type of assay used to measure estradiol, progesterone, testosterone, follicle stimulating hormone, and/or estriol levels in the body fluid of a menopausal woman. Any of the current assays for hormone analysis can be used, as well as assays that may be developed in the future. Examples of such assays are described in detail below.

The assay can be carried out on any sample of body fluid, such as blood (or a blood fraction, especially serum or plasma), urine, cervical or vaginal secretions, sweat, or saliva. Saliva is preferred for simplicity of sampling.

A "sample" is the material being analyzed and is usually of direct biological origin, although pre-treatment may have removed some of the normal biological compounds normally associated with the analyte (such as red cells separated from plasma in a whole blood sample).

In the broader aspects of the invention, there are no limitations on the collection and handling of body fluid samples as long as consistency is maintained. With some body fluids, such as saliva and plasma, there is little diurnal variation in hormone levels. For other fluids, notably urine, variations occur, and it is preferred to eliminate variations to the extent possible, for example by taking samples at the same time of day. However, other techniques can be utilized to ensure consistency of measurement of analytes in clinical fluids. For example, creatinine can be measured concurrently to standardize hormonal assays in urine. Creatinine is produced at a constant rate in the kidneys, and measurement of creatinine concentration allows correction of volume errors in urine samples, as is well known in the art.

In preferred embodiments, hormonal levels are measured as discussed above, and modification of the dosage is prescribed if the hormonal levels are found to deviate from the following optimal ranges (In Clinical Gynecologic Endocrinology and Infertility, 4th edition, ed. Speroff et al., Williams and Wilkins (Baltimore, MD), p. 629 (1989); In Tietz Textbook of Clinical Chemistry, 3rd ed., W. B. Saunders and Co. (Philadelphia, Pa.), pp. 1811–1814; 1831–1835; 1999):

| Hormone | Source | Optimal Range |
| --- | --- | --- |
| Estradiol | Blood | 5 pg/ml to 600 pg/ml |
| Estradiol unconjugated | Urine | 4–20 pg/ml |
| Estrogens (total) | Blood | 100–400 pg/ml |
| Estrogens (total) | Urine | 15–80 pg/ml |
| Estrone (unconjugated) | Blood | 0.4 to 25 ng/ml |
| Estrone (unconjugated) | Urine | 10 to 35 ng/ml |
| Progesterone | Blood | 15 ng/dL to 2500 ng/dL |
| Testosterone (total) | Blood | 15 ng/dL to 80 ng/dL |
| Follicle stimulating hormone (FSH) | Blood | 1 to 19 mIU/ml |
| FSH | Urine | 2 to 15 IU/d |

According to the methods of the invention, it is assumed that salivary hormone levels (and thus optimal salivary hormonal levels) are approximately 10% of blood levels.

Because of the many different possible clinical goals, the actual hormonal level indicative of effective menopausal treatment, and the modifications to therapy, are best selected by the attending physician.

It will be recognized by those skilled in clinical analysis that instant assays for a given hormone are not expected to be obtained or to be interpreted by an attending physician in the absence of additional information, but can be used by a skilled medical practitioner in combination with other information to monitor the effectiveness of HRT.

In a preferred embodiment, standard enzyme immunoassays are used to measure hormonal levels. In a typical assay using this technique, the enzyme-labeled, competitive binding component comprises estradiol, testosterone, progesterone, and/or estriol (or the portion thereof used to generate the antibody used in the assay) bound to the immunogen that is used to produce the antibody of the assay. An enzyme label is bound to this moiety, preferably through a bulky linker such as an avidin-biotin complex. The use of such a competitive binding compound allows antibodies to be used without attempting to manipulate affinity of binding of antibody to competitor while still providing the steep competitive binding curve required for such an analysis.

In a typical such assay, antibody is attached to a solid surface, such as a microtiter plate well, a test tube, or a porous reagent strip (such as cellulose or glass fibers). The antibody-coated solid surface is then contacted simultaneously with a sample and with a competitive binding compound. By providing fewer antibody binding sites than are present in the combined total of analyte and competitive binding compound, only a fraction of the molecules in solution will bind to the solid surface. If there are no analyte molecules present, all of the binding sites will be taken up by the competitive binding compounds so that a maximum amount of enzyme is attached to the solid surface. When a substrate for the enzyme is contacted with the solid surface after the sample is washed away, reaction of the enzyme with the substrate provides a detectable signal (usually formation of a color) that indicates to the user the absence of analyte in the sample (a negative result). If the analyte is present in the sample, analyte competes for binding sites so that less of the enzyme-labeled competitor can bind. By using a bulky binding composition, which binds less rapidly to the antibody than does the analyte, and by properly selecting the number of binding sites relative to the amount of sample added (which is a standard technique to one of skill in the art), analyte present at a concentration above a pre-selected minimum level will exclude binding of the competitive binding composition and thus binding of the enzyme to the solid substrate. Thus, if sufficient analyte is present in the sample, no enzyme is present after the reaction to produce a color change, and thus the reaction mixture stays the same color (i.e.: a positive reaction using this reaction scheme).

Other reaction schemes can be used in which the formation of color is indicative of the presence of the analyte. The previous example is merely one of many types of competitive binding assays in which estradiol, testosterone, progesterone, and/or estriol can be measured.

Antibody production for use in an assay for estradiol, testosterone, progesterone, and/or estriol is conventional and is not described here in detail. Techniques for producing antibodies are well known in the literature and are exemplified by the application Antibodies: A Laboratory Manual (1988) Eds. Harlow and Lane, Cold Spring Harbor Laboratories Press, and U.S. Pat. Nos. 4,381,292, 4,451,570, and 4,618,577. For an example of production of antibodies specific for estradiol, see Lasley et al., Fertility and Sterility (1985) 43:861–867, and Munro et al., Abstract, Society for Gynecologic Investigation, San Diego, March 1989. The same techniques can be used to produce antibodies to testosterone, progesterone, and/or estriol. A brief discussion of general techniques for the production of antibodies specific for steroids is included for those who may be unfamiliar with the process.

An animal is injected with a composition containing the hormone of interest covalently attached to an immunogen, usually a protein, prepared as described above. Multiple injections or the use of an adjuvant will ensure maximum stimulation of the immune system and production of antibodies. If polyclonal antibodies are desired, they can be prepared by simply collecting blood from the immunized animal and separating the antibodies from other blood components by standard techniques. To obtain monoclonal antibodies, the spleen or lymphocytes from the immunized animal are removed and immortalized or used to prepare hybridomas by cell-fusion methods known to those skilled in the art. Antibodies secreted by the immortalized cells are screened to determine the clones that secrete antibodies of the desired specificity. For monoclonal anti-estriol antibodies, the antibodies must bind to estriol. Cells producing antibodies of the desired specificity are selected, cloned, and grown to produce the desired monoclonal antibodies.

Antibody can be attached to a solid surface for use in an assay of the invention using known techniques for attaching protein material to solid support materials. The solid support can include plastic surfaces of test tubes or microtiter plates, polymeric beads, dip sticks, or filter materials. The attachment methods include non-specific adsorption of the protein to the support and covalent attachment of the protein, typically through a free amino group, to a chemically reactive group on the solid support, such as an activated carboxyl, hydroxyl, or aldehyde group.

In a preferred aspect of the invention, the body fluid to be tested is collected into a fluid collection kit, including but not limited to that described in U.S. Pat. Nos. 5,786,227 and 5,786,228, herein incorporated by reference in their entirety. The fluid collection kit is particularly adapted for collecting and storing viscous biologic samples, such as saliva, in the inner tube after the sample has been mixed with a preservative or other substance located in the filter, such as a dye or protease inhibitor.

Any number of materials can be present on the filter so that they will mix with the sample, depending on the particular sample being collected. For biological samples, this will generally include a preservative. Examples of preservatives include sodium azide ($NaN_3$) and Proclin™. A particularly preferred preservative for saliva is thimerosal. The general operating characteristics of the preservatives are that they be soluble in the fluid with which they are to be mixed and be sufficiently stable to storage under the conditions under which the collection kit will be used. Since these conditions will vary with the sample and with the manner in which sample is collected, a wide variety of agents can be used. For example, a collection kit designed for home use can be refrigerated, which will provide for relatively mild storage conditions and allow reasonably delicate preservatives to be used. A test kit designed for field operation may be subject to a variety of different temperatures and humidities and thus would restrict the preservatives used in such a kit.

Other materials that can be present on the filter include a dye, which makes it possible to readily determine whether uniform mixing has taken place. Examples of dyes include any of the numerous standard dyes set forth in standard dye catalogues, selected to be soluble in the material being collected. A dye particularly useful for saliva collection is FDNC Blue #1. The essential characteristic of the dye is that it be soluble in the liquid being collected.

The individual collection apparatuses of the invention can be stored in a fluid collection kit comprising multiple tubes of the two types described above and multiple caps. The kit will normally comprise a container adapted to hold the tubes and caps in a readily accessible manner (typical of the type used in a test tube rack in which the individual tubes are inserted into holes in a rack-like device, typically made of cardboard in a commercial collection kit). The individual tubes can have built-in labels for ease of use (for example, containing spaces for patient name and date and time of collection), and written instructions adapted for the particular type of sample can be included in the box that holds the individual tubes.

The instant invention further provides kits for monitoring the effectiveness of hormone replacement therapy in a early menopausal or late menopausal woman, comprising a fluid collection device, such as those described above, and instructions for using the fluid collection device for monitoring the effectiveness of hormone replacement therapy in a menopausal woman by using the methods of the invention described above.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. A method for monitoring the effectiveness of hormone replacement therapy in a perimenopausal woman, comprising
   a. obtaining a body fluid sample from the perimenopausal woman;
   b. testing for hormonal levels in the body fluid of the perimenopausal woman at intervals of between about 7 days to about 90 days, wherein testing for hormonal levels comprises testing for levels of at least one of progesterone, testosterone, estradiol, follicle stimulating hormone, and estriol; and
   c. adjusting levels of replacement hormone administered to the woman based on the test results.

2. A method for monitoring the effectiveness of hormone replacement therapy in a early menopausal or late menopausal woman, comprising:
   a. obtaining a body fluid sample from the perimenopausal woman;
   b. testing for hormonal levels in the body fluid of the perimenopausal woman at intervals of between about 30 days to about 180 days, wherein testing for hormonal levels comprises testing for levels of at least one of progesterone, testosterone, estradiol, follicle stimulating hormone, and estriol; and
   c. adjusting levels of replacement hormone administered to the woman based on the test results.

3. The method of claim 1 wherein the body fluid is saliva.

4. The method of claim 2 wherein the body fluid is saliva.

5. A kit for monitoring the effectiveness of hormone replacement therapy in a perimenopausal woman, comprising:
   a. a fluid collection device;
   b. instructions for using the fluid collection device for monitoring the effectiveness of hormone replacement therapy in a menopausal woman according to the method of claim 1.

6. A kit for monitoring the effectiveness of hormone replacement therapy in a early menopausal or late menopausal woman, comprising:
   a. a fluid collection device;
   b. instructions for using the fluid collection device for monitoring the effectiveness of hormone replacement therapy in a menopausal woman according to the method of claim 2.

* * * * *